Figure 1:
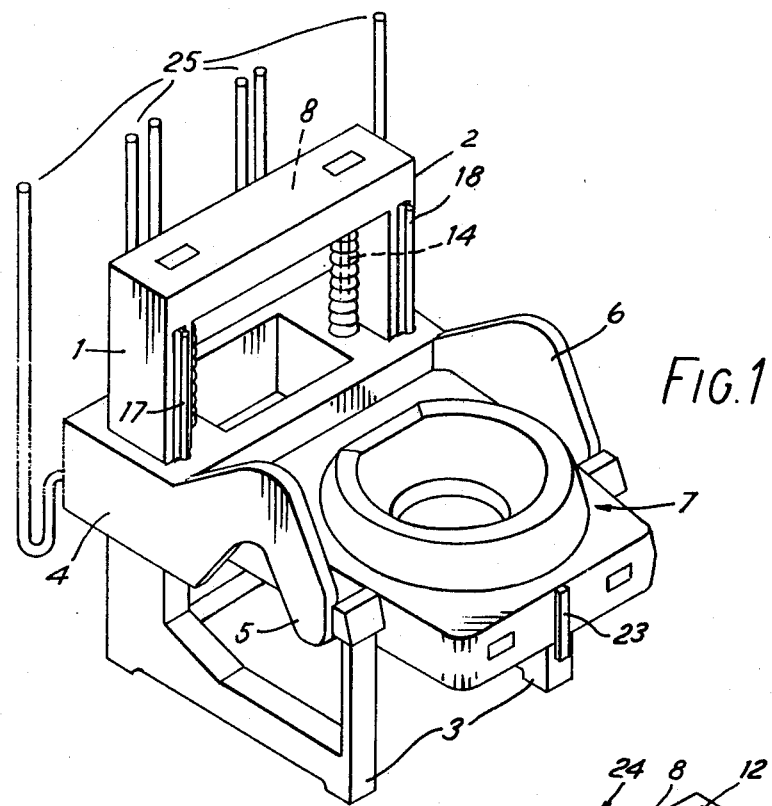

United States Patent [19]
Bernardi

[11] 4,316,091
[45] Feb. 16, 1982

[54] CT SCANNER

[75] Inventor: Richard T. Bernardi, Prospect Heights, Ill.

[73] Assignee: EMI Limited, Middlesex, England

[21] Appl. No.: 94,723

[22] Filed: Nov. 15, 1979

[51] Int. Cl.³ ............................................ G01N 21/34
[52] U.S. Cl. ................................................ 250/445 T
[58] Field of Search ................................... 250/445 T

[56] References Cited

U.S. PATENT DOCUMENTS

| | | | |
|---|---|---|---|
| 2,281,931 | 5/1942 | Frank | 250/445 T |
| 3,778,614 | 12/1973 | Hounsfield | 250/445 T |
| 3,924,129 | 12/1975 | LeMay | 250/445 T |
| 4,000,425 | 12/1976 | Craig | 250/445 T |
| 4,063,097 | 12/1977 | Barrett et al. | 250/445 T |
| 4,115,695 | 9/1978 | Kelman | 250/445 T |
| 4,137,455 | 1/1979 | Fetter | 250/445 T |
| 4,139,775 | 2/1979 | Williams | 250/445 T |

*Primary Examiner*—Davis L. Willis
*Attorney, Agent, or Firm*—Cooper, Dunham, Clark, Griffin & Moran

[57] ABSTRACT

A CT scanner is described in which the data acquisition components, i.e. the radiation source and detectors, are mounted in an apertured housing which can be deployed generally vertically, for the examination of recumbent patients, or generally horizontally, for the examination of patients seated, or standing, with their torsos upright.

10 Claims, 5 Drawing Figures

CT SCANNER

The present invention relates to CT Scanners. Such scanners have been in use since about 1972 and provide representations of the variation with position of X-ray absorption over thin cross-sectional slices of patients' bodies. These representations are generally accepted to be of clinical value to the diagnostician, and it is not uncommon that these representations can be obtained without hospitalization of, or discomfort to, the patient.

CT Scanning was invented by Godfrey N. Hounsfield, of the English firm EMI Limited (the assignee of this application) and is described, inter alia, in his U.S. Pat. No. 3,778,614. The technology of CT scanning, in brief, involves the acquisition of data indicative of the attenuation suffered by X-radiation when projected across a cross-sectional body slice along each of many substantially linear paths from many different directions, and the compensated back-projective processing of the acquired data to produce the required representation.

Due to the valuable clinical impact which CT scanning has made, much effort and expense has been put into developing the technology, and especially into speeding up the data acquisition rate. One of the more recent inventions in that area is described and claimed in Richard W. Fetter's U.S. Pat. No. 4,137,455. Considerable interest has also been shown in improving the speed and accuracy with which the acquired data are processed. U.S. Pat. No. 3,924,129 to Christopher A. G. Lemay describes and claims improved technology for effecting such processing.

One thing that has remained unchanged hitherto, however, is the requirement for the patient to be presented to the machine lying prone or supine on a horizontal patient handling system. It is an object of this invention to provide a CT scanner which is additionally capable of examining patients in attitudes other than recumbent. In particular, it is an object of this invention to provide a CT scanner which is capable of scanning patients sitting or standing with an upright torso.

Figure 2:
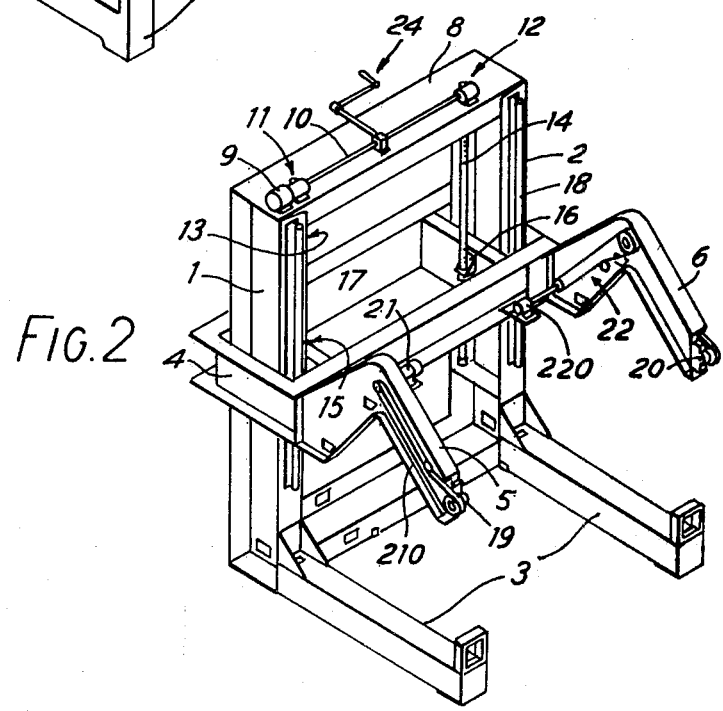
Figure 3:
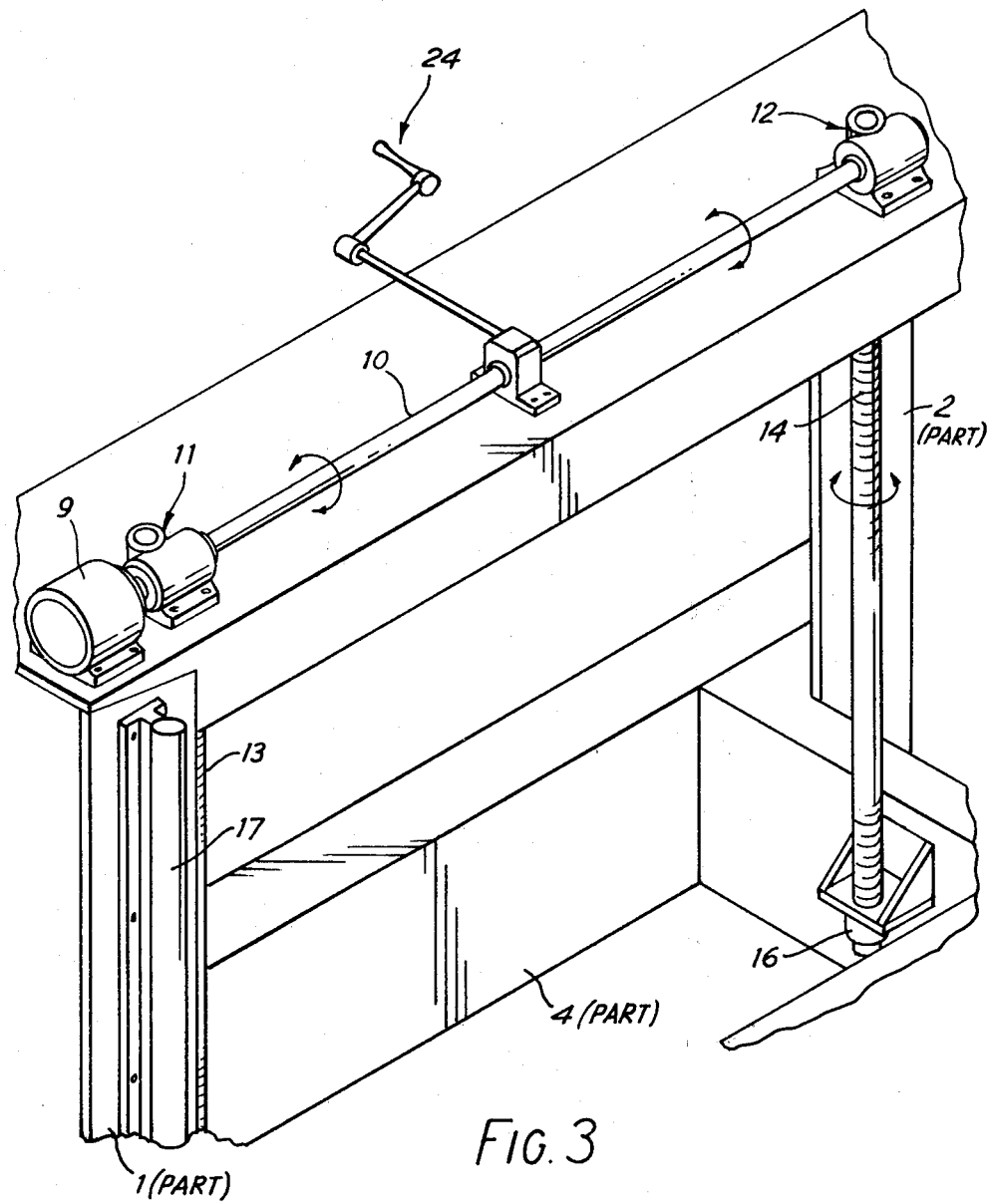
Figure 4:
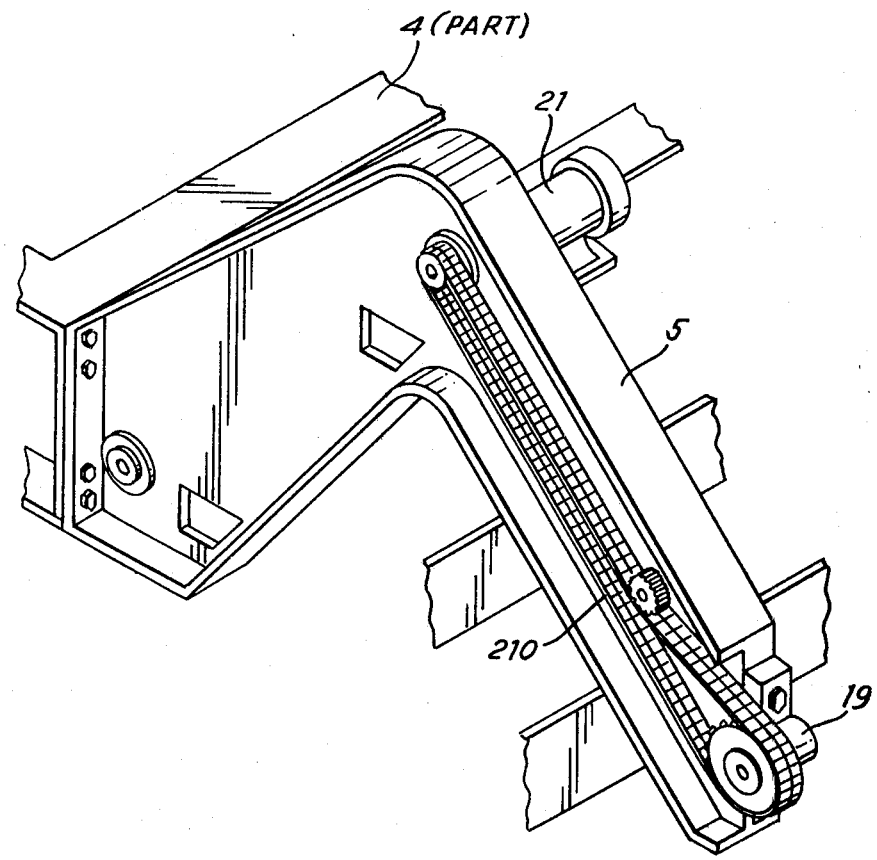
Figure 5:
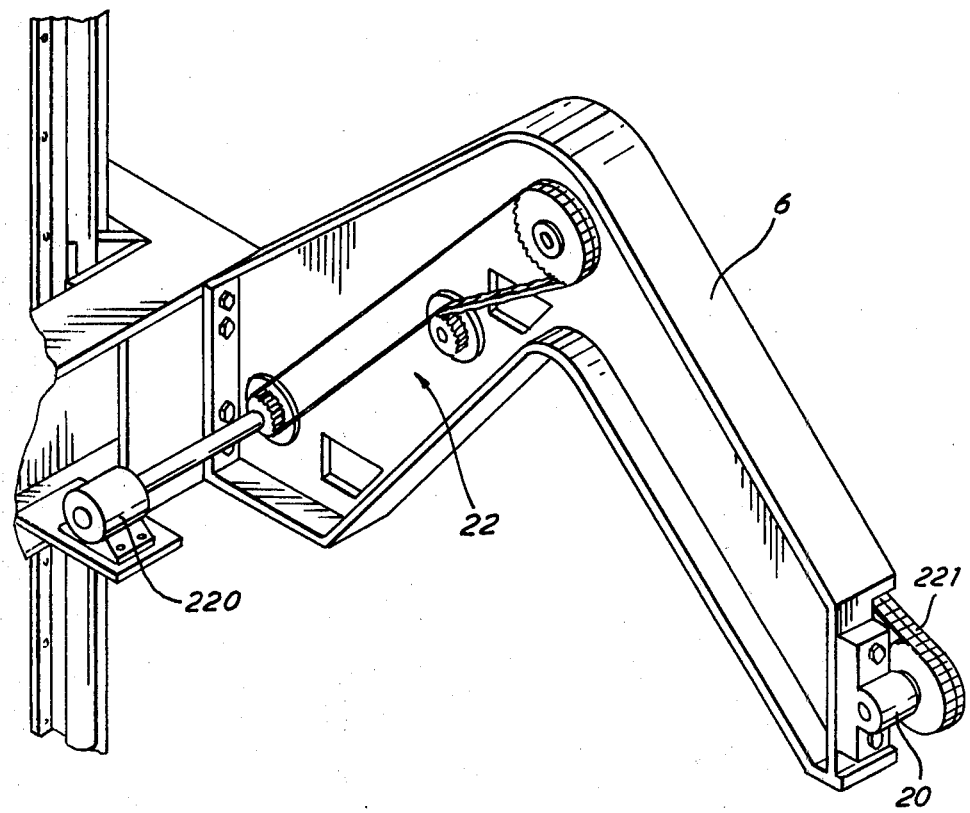

In order that the invention may be clearly understood and readily carried into effect, one embodiment thereof will now be described, by way of example only, with reference to the accompanying drawings of which:

FIG. 1 shows, in perspective view, a CT scanner in accordance with one example of the invention, FIG. 2 shows, in the same general perspective view as FIG. 1, some mechanical details used in the embodiment, and FIGS. 3, 4 and 5 show, on expanded scale, certain important features of the FIGS. 1 and 2 embodiment.

Referring now to the drawings, the CT scanner shown therein comprises, basically, a pair of uprights 1, 2 secured to a base unit 3. A yoke 4, surrounding the uprights, carries a pair of side-arms 5, 6 between which is located the source and detector unit, within a housing part schematically shown at 7 in FIG. 1. A top crossmember 8 for the uprights supports an electric motor 9 which drives a mechanism, including a drive rod 10, a pair of right-angle jacks 11, 12 and a pair of machine screws 13, 14 with travelling nut assemblies 15, 16 for raising and lowering the yoke 4. The yoke 4 runs on suitable linear bearings, such as 17, 18 formed on the uprights 1, 2.

The side arms 5, 6 carry, at their ends, respective trunnions 19, 20 on which the source/detector unit, in casing part 7, can rotate. The rotation could be achieved manually but in this example of the invention it is effected mechanically by means of a second electrical motor 21 which drives, via a chain arrangement 210, the trunnion 19. A fail safe brake arrangement 22, is provided in the side arm 6 to ensure that the tilting of the housing part 7 and its contents is effected in a controlled manner.

In this example, the CT scanner, apart from the invention, is similar to the scanner described and claimed in the aforementioned U.S. Pat. No. 4,137,455. Thus the source rotates, within the housing part 7, about an axis which passes centrally through the aperture in said housing part and the detectors nod, or nutate, in a direction parallel to that axis but do not rotate with the source.

In practice, depending upon the attitude which is considered to be of most comfort, or promises to give rise to the best representations, the patient may be disposed recumbent or upright; the housing part 7 being driven to the required attitude by means of the motor 21 and its associated components, FIGS. 3 through 5 show, on a scale much enlarged with respect to FIGS. 1 and 2, various of the mechanisms briefly described hereinbefore.

FIG. 3 shows, primarily, the arrangement for adjusting the height of the yoke 4 on the uprights 1 and 2. The object of using the double upright system with a closed yoke is to render the housing 7 highly stable and to ensure that only minimal stresses are applied to the main frame of the gantry housing as a result of system twist. Each of the two uprights 1 and 2 has its own rotating machine screw (13 and 14) with travelling nut (15 and 16). The objective of using machine screws is to eliminate system backdriving. This is possible because the machine screws are self-locking devices. Thus this provides patient safety during power down conditions. The objective of using two screws is that each of the machine screws is capable of holding the entire system load. Thus, if a screw fails, the other can take the load and provide added patient safety. The yoke 4 is supported by four sets of linear bearings (such as 17) on each upright, and the system is designed so that if one bearing fails, the others can take the load.

The arrangement as shown, wherein the yoke encloses the uprights, is also preferred because it ensures parellism and perpendicularity of the arrangement as a whole while in service. A yoked system also permits the use of simple arrangements for handling the various cables 25 that are employed as is shown in FIG. 1.

FIG. 3 shows how the motor 9 transmits its drive, via rod 10 and the two right-angle jacks 11 and 12, to the machine screws 13 and 14. Manual elevation adjustments of the housing 7 (From FIG. 1) can be accomplished by using the hand crank 24 in case of power failure.

FIG. 4 shows the side-arm 5 and its attachment to the yoke 4, and illustrates in particular the chain drive arrangement 210, operated by motor 21, which is used in this example of the invention to rotate the trunnion 19 which supports one side of the housing part 7 (FIG. 1) so as to rotate the housing part 7 relative to the remainder of the machine. The apertures formed in the side arm are utilized for cable ducting.

FIG. 5 shows the other side arm 6 and indicates how an idler chain arrangement 221 thereon, which is driven by movement of the housing part 7, referred to earlier and produced by the arrangement shown in FIG. 4, is coupled (via a chain drive system 222) to a fail-safe brake 220. The brake 220 utilizes ceramic magnets and is engaged in the power-down condition. This brake will also engage if the gantry begins tilting at an excessive rate or if no load is applied to the running motor. The brake 220 is a redundant safety device because the tilt motor 21 (in FIG. 2) has a built in self-locking speed reducer which protects the patient during power down.

For added safety, a hand crank 24 can be used to raise the housing without power.

Returning to FIG. 1 finally, a laser alignement system that can take any convenient form is shown at 23.

Thus, in summary, it will be evident that the invention resides in providing a CT scanner with the facility of examining patients in a horizontal (lying) or vertical (seated or standing) attitude. It has already been proposed to provide means for tilting the gantry relative to the patient. U.S. Pat. No. 4,139,775, for example, discloses such an arrangement, but such tilts as have been provided hitherto have been relatively small angular tilts about the conventional (vertical) gantry position, and could not accommodate a patient in a sitting or standing attitude.

It will be appreciated that investigation of a patient with his or her torso generally upright can enable certain organs to be examined more easily because other organs which might be pressed against the organ in question with the patient lying on a bed might sag away from the organ in question when the patient's torso is upright. It will also be appreciated for radio therapy applications that require the treatment of a patient in the vertical attitude. Radiotherapy requires that the organs be in the same position during CT scanner diagnosis and radiotherapy planning as they would be during treatment. Also, examination with an upright torso can be advantageous for patients with a tendency to become nauseous in the recumbent attitude.

It will also be appreciated that the invention is not limited to the specific embodiment thereof described hereinbefore. For example, it will be readily apparent that the side arms 5 and 6 need not be formd in the inverted V-shape shown in the drawings. They could equally well be straight or curved. Additionally, the side arms, as well as other load-bearing components, might be formed with apertures, or even constructed of welded girders, castings or the like, for extra strength.

What we claim is:

1. A CT scanner having an aperture housing containing data acquisition components for acquiring data relating to the attenuation suffered by X-radiation on traversing each of many substantially linear paths across a cross-sectional slice of a patient's body, a support structure supporting said housing and moving means for moving said housing relative to said support structure, said moving means disposing said housing with its aperture either generally vertical, to receive a recumbent patient, or generally horizontal, to receive an upright patient.

2. A scanner according to claim 1 wherein said support structure comprises a yoke and a pair of side arms supported by said yoke, said side arms bearing at their unsupported ends, rotatable support members, and said apertured housing being spported by said support members.

3. A scanner according to claim 2 wherein said support structure further includes a base unit, and a pair of uprights secured to said base unit, and wherein said yoke encloses said uprights.

4. A scanner according to claim 3 including control means for moving said yoke up and down relative to said uprights.

5. A scanner according to claim 4 wherein said control means includes a motor, a pair of machine screws, rotatable but otherwise fixed in relation to said uprights, co-operating with travelling nuts which are captive relative to said yoke, and drive transmitter means for transmitting the motor drive in parallel to said machine screws.

6. A scanner according to claim 2 wherein said means for moving comprises a motor driven chain mechanism mounted in one of said side arms and disposing the respective rotatable support members associated with said side arm.

7. A scanner according to claim 6 wherein said means for moving further includes a fail-safe brake unit mounted in the other of said arms and coupled to the rotatable support member associated with said other arm.

8. A scanner according to claim 1 including a laser unit, supported by said housing, positioned to project a desired light pattern on the patient's body.

9. A CT scanner as in claim 1 in which said means for moving the housing comprise means for selectively moving said housing relative to said support structure both vertically and rotationally.

10. A CT scanner including a housing part formed with an aperture dimensioned to accommodate a patient's body, said housing part containing a radiation source and an associated detector unit for the acquisition of measurements of the amounts of radiation transmitted from the source, across a cross-sectional slice of the patient's body, to the detector unit along many substantially linear paths in the plane of the slice, the source at least being capable of angular movement around the patient's body about an axis which intersects said slice and extends generally longitudinally of the patient's body, a support structure supporting said housing part for pivotal movement, about a second axis substantially parallel to said slice and substantially orthogonal to the first-mentioned axis, and moving means effecting said pivotal motion and causing, prior to the patient being disposed in said aperture, the housing part selectively to assume one of two pivotal conditions, one of said conditions accommodating recumbent patents and the other of said conditions accommodating upright patients.

* * * * *